United States Patent [19]

Ahlberg et al.

[11] Patent Number: 4,880,076

[45] Date of Patent: Nov. 14, 1989

[54] HEARING AID EAR PIECE HAVING DISPOSABLE COMPRESSIBLE POLYMERIC FOAM SLEEVE

[75] Inventors: Carl S. Ahlberg, Minneapolis; Davis W. Chamberlin; Jerold W. Bushong, both of St. Paul; Robert J. Oliveira, Maplewood; Vasant V. Kolpe, Mendota Heights, all of Minn.

[73] Assignee: Minnesota Mining and Manufacturing Company, St. Paul, Minn.

[21] Appl. No.: 938,540

[22] Filed: Dec. 5, 1986

[51] Int. Cl.[4] .......................... A61B 7/02; H04R 25/02

[52] U.S. Cl. .................................... 181/130; 181/135; 381/68.6

[58] Field of Search ....................... 181/130, 134, 135; 128/152; 381/68, 68.5, 68.6, 68.7

[56] References Cited

U.S. PATENT DOCUMENTS

| | | | |
|---|---|---|---|
| Re. 29,487 | 12/1977 | Gardner, Jr. | 128/152 |
| 789,876 | 5/1905 | Pape . | |
| 1,753,817 | 4/1930 | Aber | 181/130 |
| 1,830,198 | 11/1931 | French | 181/135 |
| 3,169,600 | 2/1965 | Thomas | 181/135 |
| 3,415,246 | 12/1968 | Hill | 181/130 X |
| 3,539,032 | 11/1970 | Scanlon | 181/135 |
| 3,783,864 | 1/1974 | Moller | 128/152 |
| 3,882,848 | 5/1975 | Klar et al. | 181/135 X |
| 3,895,627 | 7/1975 | Leight | 128/152 |
| 4,253,452 | 3/1981 | Powers et al. | 128/152 |
| 4,375,016 | 2/1983 | Harada | 181/135 |
| 4,407,389 | 10/1983 | Johnson | 181/130 X |
| 4,552,137 | 12/1985 | Strauss | 128/152 |
| 4,677,679 | 6/1987 | Killion | 381/74 |
| 4,724,922 | 2/1988 | Kalayjian | 181/135 |

FOREIGN PATENT DOCUMENTS 1395197 3/1965 France .

OTHER PUBLICATIONS

Berger, E. H. (1976), "Can Hearing Aids Provide Hearing Protection", Hearing Instruments 38(3), 12–14.

Navarro, M. R. (1978), "Reducing Feedback During the Hearing Aid Evaluation", Audiology & Hearing Educ. 4(6), p. 15.

Frank. T. (1980), "Attenuation Characteristics of Hearing Aid Earmolds", Ear and Hearing 1(3), 161–166.

Killion, M. C. (1981), "Earmold Options for Wideband Hearing Aids", J. Sp. Hearing Disorders 46(1), 10–20.

Gerling, I. J. and Roeser, R. J. (1981), "A Modified Foam Earplug for the Hearing Aid Evaluation", Ear and Hearing 2(2), 82–87.

*Primary Examiner*—Benjamin R. Fuller

*Attorney, Agent, or Firm*—Donald M. Sell; Walter N. Kirn; James V. Lilly

[57] ABSTRACT

Detachably secured to the ear piece of a hearing aid is a user-disposable sleeve comprising soft polymeric retarded recovery foam that can be compressed to be freely insertable into a person's ear canal and then allowed to recover to become wedged in the canal. The sleeve preferably includes a flexible, elongated plastic duct over which the foam fits, and the duct is formed with a screw thread of a rigid plastic which mates with a screw thread on the ear piece for easy attachment and removal. The external surface of the foam preferably is substantially cylindrical and can be formed with flutes to provide venting of the user's ear.

43 Claims, 3 Drawing Sheets

HEARING AID EAR PIECE HAVING DISPOSABLE COMPRESSIBLE POLYMERIC FOAM SLEEVE

BACKGROUND OF THE INVENTION

1. Field of the Invention

The invention relates to the ear piece of a hearing aid, namely the portion which is inserted into the external ear canal. The ear piece may be the hearing aid itself, for example, a canal hearing aid or an in-the-ear hearing aid; or an attachment, such as the end of a flexible sound tube of a behind-the-ear hearing aid. The ear piece often is molded to fit an individual's ear canal and sometimes has a compressible, resilient sleeve for enhanced comfort. Such a sleeve is often employed to permit one or a few ear pieces to fit nearly everyone, as do ear pieces of the invention.

2. Description of the Related Art

The problem of providing a hearing aid with an ear piece that can be continuously worn with comfort has long been a subject of research. See, for example, U.S. Pat. No. 1,743,817 (Aber). There, an impression of an individual's ear canal was used to mold an ear piece (there called an "audiphone cap"). Such a procedure is still in widespread use, even though time-consuming and expensive and requiring two visits to fit a person with a hearing aid. Moreover, the resulting ear piece is rigid, uncomfortable to wear, and prone to falling out of the ear canal.

U.K. Patent Application No. 2,091,063 (Blackstone) discloses the use of a layer of cushioning material, preferably one providing a high coefficient of friction, to seal a small gap between the external surface of a molded ear piece (called a "plastics molded component") and the internal surface of the ear canal, and to eliminate any whistling sound or echo effect. The molded ear piece approximates the shape of the external ear canal. Only a thin layer of the cushioning material is employed with the result that it does not provide a truly comfortable fit.

FIGS. 14–18 of U.S. Pat. No. 4,375,016 (Harada) show a layer of cushioning material in the form of a sleeve which fits over the distal end of the ear piece and is said to provide excellent fit without the necessity of using a custom molded construction. That sleeve is "formed from a compressible foam with characteristics as shown in U.S. Pat. No. Re. 29,487." The foam "can be compressed to a diameter less than that of the auditory canal. As the foam slowly attempts to return to its original configuration, it seals the auditory canal in a comfortable fashion as shown in FIGS. 17 and 18" (Col. 4, lines 41–56). However, the Harada patent does not indicate how the sleeve is prevented from remaining in the ear canal if the ear piece is either accidentally dislodged from the ear canal or simply pulled out. Rather than dealing with such matters, the Harada patent concentrates on the venting of excess sound pressure from the ear canal to the atmosphere.

The reissue patent (Gardner, Jr.) cited in the Harada patent does not concern hearing aids but describes an "earplug . . . composed of a resilient, plasticized polymeric foam containing a sufficiently high concentration of organic plasticizer to provide the foam with a rate of recovery from 60 percent compression to 40 percent compression in from 1 to 60 seconds and an equilibrium pressure at 40 percent compression thereof from 0.2 to 1.3 p.s.i." (claim 1). Cylindrical plugs of this material can be coaxially bored and employed as a covering over a tubular tip portion of a lightweight headphone set. However, like the Harada patent, Gardner does not indicate how the plug is prevented from remaining in the ear canal if the tubular tip portion is accidentally dislodged or simply pulled out.

Despite the approaches discussed above, none have been truly effective, particularly from the standpoint of providing an ear piece which is comfortable, retained during use, and readily removable when desired. Moreover, none have addressed a continuing problem in the hearing aid art, namely clogging of the sound tube by ear wax. Approximately half of professional repairs of hearing aids are either to remove ear wax or to repair damage caused by a user who tried to clean out the wax. That problem has been addressed in U.K. Patent Application GB 2,155,276A (Brander et al.); West German Offenlegungsschrift 2,818,273 (Sommer); and EPO Patent Application 85103722.6 (Laid open No. 0,159,571) (Moser et al.).

SUMMARY OF THE INVENTION

The present invention provides, in one aspect, a user-disposable attachment to a hearing aid that should enables the user to keep its ear piece clean with only minimal, if any, risk of damage to the hearing aid. Moreover, hearing aids utilizing this disposable sleeve enable the user to hear better, that is hear better quality sound. The novel user-disposable attachment comprises a sleeve which can be used with an in-the-ear hearing aid, a behind-the-ear hearing aid, or a canal hearing aid. The novel sleeve is:

(1) easy to use,
(2) easy to change,
(3) comfortable to wear due to its conformability and yet reliably stays in place,
(4) easy to manufacture, and
(5) conveniently fitted by an audiologist to almost any user.

Furthermore, by selecting from a set of sleeves of the invention, the audiologist will be able to provide each user with the best possible acoustical fit.

In another aspect, the invention provides a hearing aid comprising an ear piece through which a sound tube extends plus a sleeve which is formed with a central longitudinal passage approximating the size of the sound tube. The sleeve comprises soft polymeric foam that has retarded recovery. That is, while being highly compressible, it has slow, substantially complete recovery, and can be compressed to be freely insertable into a user's external ear canal to become wedged in the canal when the foam is allowed to recover.

These retarded recovery attributes also are possessed by the foam sleeve of the hearing aid of FIGS. 14–18 of the above-cited Harada patent. Unlike that of the Harada patent, the sleeve of the present invention is user-disposable and the hearing aid of the invention includes means for disposably attaching the sleeve to the ear piece. When attached, said central longitudinal passage of the sleeve connects the sound tube to the user's ear. The attaching means should provide a Holding Value at least $1\frac{1}{2}$ times the Pullout Value, each of which terms is defined hereinbelow. At substantially lower ratios of Holding Value to Pullout Value, there is a danger that the polymeric foam sleeve will be left in the person's ear canal if the ear piece were accidentally dislodged or otherwise pulled out.

The exterior surface of the novel sleeve preferably is substantially cylindrical, tapering slightly inwardly toward its distal end to enhance insertion into the user's ear canal. The sleeve may be formed either by molding or by cutting a section from a block. If the sleeve is molded, the exterior surface may possess a skin of higher density cell structure than that of the interior of the sleeve. This skin may minimize ear wax penetration of the foam; provide water resistance to the foam; and generally improve the cleanliness of the foam.

To remove the novel hearng aid from the ear canal, the user may first wiggle the ear piece laterally to compress the foam of the sleeve, thus reducing the friction against the wall of the canal during removal.

In addition to its sound tube, the ear piece of a canal or an in-the-ear hearing aid usually is formed with one or more air vents, in which event the sleeve may be formed with air vents connecting one or more of those air vents to the inner reaches of the ear canal. When used with a behind-the-ear hearing aid, the air vents may open to the atmosphere. The air vents preferably are provided by flutes formed in the exterior surface of the polymeric foam of the novel sleeve, usually two, three or four flutes symmetrically positioned around the exterior surface. When the exterior surface of the sleeve is substantially cylindrical, each flute preferably is semicylindrical, from 2 to 3 mm in breadth, and extends 1.0 to 1.5 mm beneath the substantially cylindrical surface.

To simplify changing sleeves by the user, the means for disposably attaching the sleeve preferably includes a duct over which the retarded recovery foam fits and to which the foam is firmly secured. When the sleeve includes a duct, the central longitudinal passage of the sleeve is provided by the duct. The duct preferably comprises a moldable plastic that is flexible to allow it to conform to the user's external ear canal and to minimize any hazard of scratching or otherwise irritating the user's ear. Preferred materials from which a flexible plastic duct may be molded include a filled or unfilled semi-crystalline polymer such as plasticized poly(vinyl chloride) or crosslinked natural or synthetic elastomers such as natural rubber, chlorinated isoprene, silicone rubber, and block copolymers of styrene-dienes. The material of the duct preferably has a Shore durometer value between 40A and 40D. The foam may be secured to the duct by a layer of adhesive cement but preferably is molded onto the duct, thus serving as its own adhesive.

The duct and the ear piece can be formed with mating screw threads which preferably are self-aligning, e.g., tapered to guard against cross-threading. This makes it easy for the user to detach a used sleeve and securely attach a fresh sleeve. When the duct comprises a flexible plastic, the portion of the duct which is threaded preferably is more rigid. When the screw threads of the duct extend beyond the proximal end of the foam, they do not interfere with the compression of the foam.

Easy attachment and detachment can also be provided by forming the duct and the ear piece to provide bayonet or ball-and-socket attachments.

A preferred retarded recovery foam for the foam sleeve is that of the "Attenutech" 6300 earplugs available from 3M. These earplugs are resilient and recover slowly from compression to provide adequate time for insertion of a compressed earplug into the external ear canal before it recovers to fill the canal. These earplugs are formed from polyurethane foam which does not contain any plasticizer. The retarded recovery foam of the Gardner patent should also be useful but less preferred because of potential problems stemming from the tendency of plasticizers to migrate and volatilize.

Preferably the compressible, soft polymeric foam of the novel sleeves has a Retarded Recovery Value (as defined below) of at least 4 seconds and no more than 45 seconds, ideally from 15 to 35 seconds. If the sleeve does not include a duct, it preferably is molded to form an impervious skin covering the walls of its central passage. Whether or not the walls of the central passage are provided by an impervious skin or a duct, those walls preferably are flared out at the distal end of the sleeve, thus minimizing the danger of blockage by ear wax.

BRIEF DESCRIPTION OF THE DRAWING

In the drawing, all figures of which are schematic,

Referring to FIGS. 1 and 2, the molded plastic casing 10 of a canal hearing aid has an ear piece 11, the external surface of which is formed with a male screw thread 12. A sleeve 13 consists of retarded recovery foam 14 and an internal, flexible, elongted plastic duct 16 formed witha longitudinal passage which provides a central passage for the sleeve 13. A substantially cylindrical layer of adhesive cement 18 secures the foam to the duct. The longitudinal passage through the duct 16 is formed with a female screw thread 20 which mates with the male screw thread 12 of the ear piece. When the sleeve 13 is threaded onto the ear piece 11, a flange 21 of its duct 16 comes to rest against the casing 10 of the hearing aid. At its distal end, the foam 14 has a flared opening 22 so that any wax from the user's ear which may accumulate on the foam is unlikely to block completely the portion of the sound tube that extends through the central passage of the sleeve 13 and connects to an internal passage 24 through the ear piece 11. When the foam is compressed to permit the assembly to be inserted into a person's ear canal and then allowed to recover to become seated, the compressive forces cannot substantially close its flared opening 22, because the foam extends only slightly beyond the distal end of the duct 16.

Figure 1:
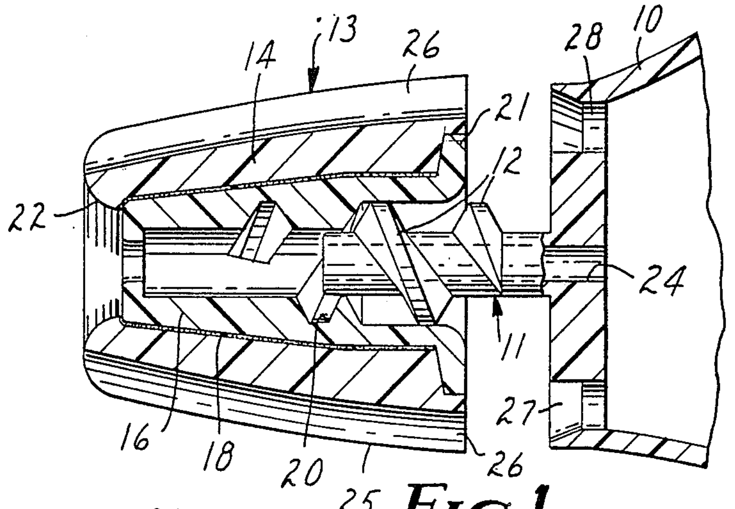
FIG. 1 is a longitudinal cross-section through a portion of a preferred hearing aid of the invention with its user disposable sleeve in position to be threaded onto its ear piece, parts thereof shown in elevation.
Figure 2:
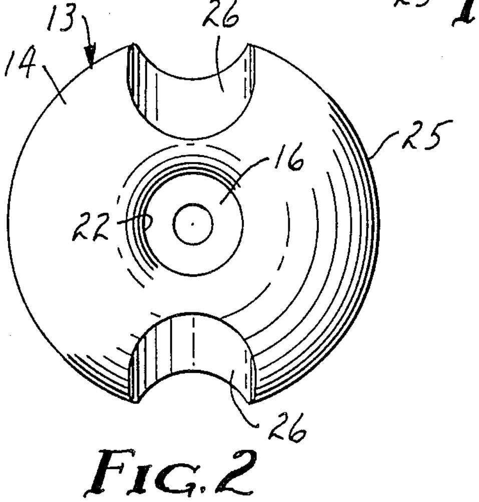
FIG. 2 is an end view of the hearing aid of FIG. 1.

The external surface 25 of the foam 14 is substantially cylindrical except for two diametrically opposed flutes 26 which, when the foam is compressed by the user's ear canal, will communicate through an annular channel 27 to a series of cylindrical air vents 28 in the casing 10 (two of which are shown), the centers of which lie substantially in a circle concentric with axis of the male screw thread 12. The substantially cylindrical surface 25 of the foam 14 tapers inwardly toward its distal end to enhance insertion into the user's external ear canal.

Figure 3:
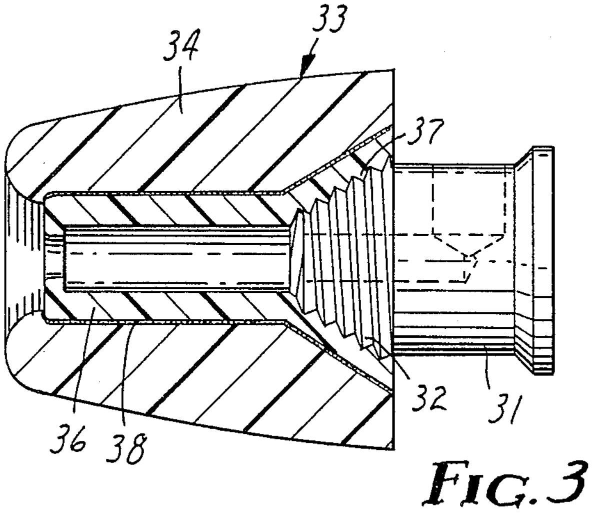
FIG. 3 is a longitudinal central cross-section through the ear piece and sleeve of another hearing aid of the invention, parts thereof shown in elevation.

Shown in FIG. 3 is an ear piece 31 of a behind-the-ear hearing aid, the distal end of which is formed with a self-aligning tapered male screw thread 32. Detachably secured to the ear piece 31 is a sleeve 33 that consists of retarded recovery foam 34, a flexible, elongated plastic duct 36, and a substantially cylindrical layer of adhesive cement 38 securing the foam to the duct. At the proximal end of the duct 36, its longitudinal passage is formed with a female screw thread 37 that mates with the male screw thread 32 of the ear piece 31.

Figure 4:
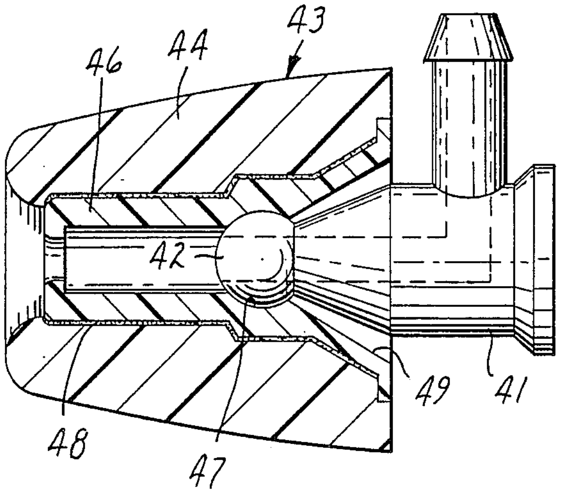
FIG. 4 is a longitudinal cross-section through the ear piece and sleeve of a third hearing aid of the invention, parts thereof shown in elevation.

Shown in FIG. 4 is an ear piece 41 of a behind-the-ear hearing aid, the distal end of which has a protuberance in the form of a ball 42. Detachably secured to the ear piece 41 is a sleeve 43 that consists of retarded recovery foam 44, a flexible, elongated plastic duct 46, and a substantially cylindrical layer of adhesive cement 48 securing the foam to the duct. The longitudinal passage through the duct 46 is formed with a socket 47 into which the ball 42 fits to permit the sleeve 43 to be readily attached or detached. The distal end 49 of the longitudinal passage of the duct 46 is conical to enhance attachment.

Figure 5:
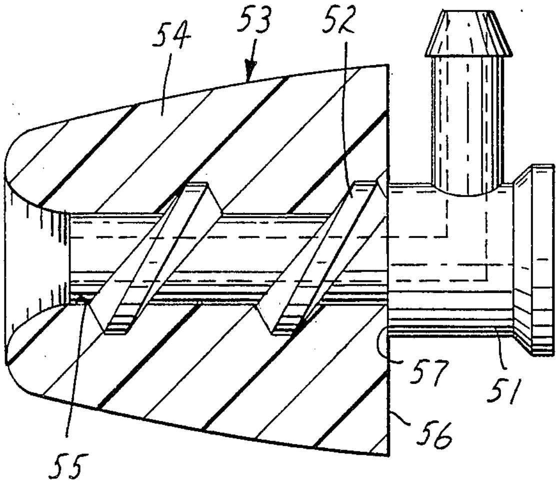
FIG. 5 is a longitudinal central cross-section through the ear piece and sleeve of a fourth hearing aid of the invention, parts thereof shown in elevation.

The behind-the-ear hearing aid of FIG. 5 has an ear piece 51, the external surface of the distal end of which is formed with a male screw thread 52, having a major diameter/minor diameter ratio of about 2. Disposably attached to the ear piece 51 is a sleeve 53 consisting of retarded recovery foam 54 formed with a cylindrical central passage 55. Because of the resilience of the foam, the sleeve has been self-threaded onto the male screw thread 52 of the ear piece 51 until its proximal surface 56 (which extends orthogonally to the axis of the passage 55) abuts the distal face 57 of the ear piece. By providing a high major diameter/minor diameter ratio, there should be no danger of leaving the sleeve in a user's ear upon withdrawing the ear piece from a wearer's ear, especially when the male screw thread is coarse and sharp.

Figure 6:
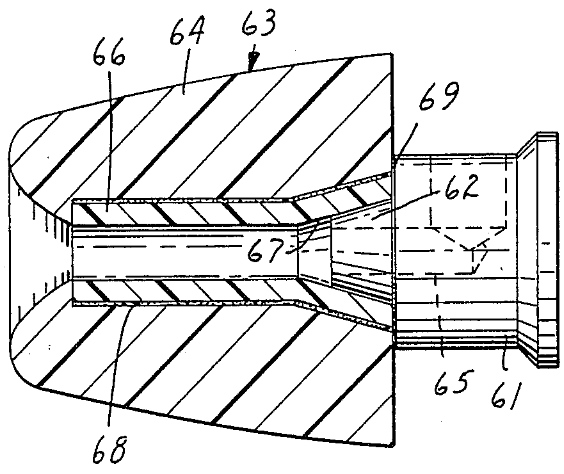
FIG. 6 is a longitudinal cross-section through the ear piece and sleeve of a fifth hearing aid of the invention, parts thereof shown in elevation.

The behind-the-ear hearing aid of FIG. 6 has an ear piece 61 which is formed with a tapered projection 62 having a central passage 65 to provide an outlet for its sound tube. Disposably attached to the ear piece 61 is a sleeve 63 consisting of retarded recovery foam 64, a flexible, elongated plastic duct 66, and a substantially cylindrical layer of adhesive cement 68 securing the foam to the duct. The proximal internal surface of the longitudinal passage 67 through the duct is tapered to mate with the projection 62. An annular layer of pressure-sensitive adhesive 69 on the proximal surface of the sleeve 63 contacts a smooth distal surface on the ear piece around its projection 62, thus releasably securing the sleeve to the ear piece.

A preferred pressure-sensitive adhesive layer 69 is "Scotch" A-60 acrylic systems No. 444 double-coated pressure-sensitive adhesive film tape from 3M.

Figure 7:
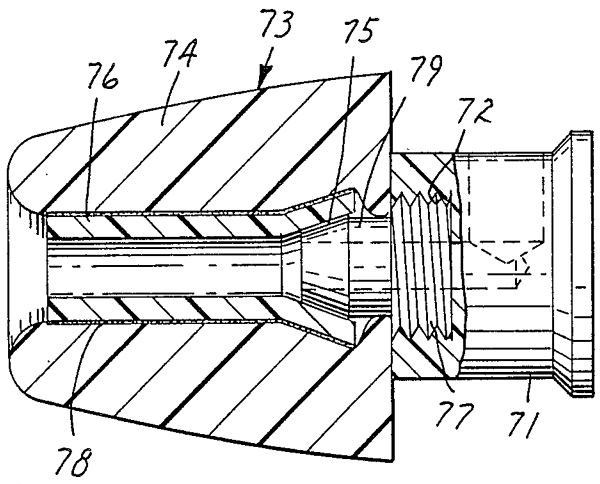
FIG. 7 is a longitudinal cross-section through the ear piece and sleeve of a sixth hearing aid of the invention, parts thereof shown in elevation.

The behind-the-ear hearing aid of FIG. 7 has an ear piece 71 which is formed with a female screw thread 72. Disposably attached to the ear piece 71 is a sleeve 73 consisting of retarded recovery foam 74, a flexible, elongated plastic duct 76, a layer of adhesive cement 78 securing the foam to the duct, and a rigid plastic adapter 79. The duct 76 and adapter 79 have been bonded together at 75 with a plastic solvent. The proximal end of the adapter is formed with a male screw thread 77 which mates with the female screw thread 72 of the ear piece 71.

Holding Value

Drilled in aluminum block 1.6 cm in thickness are a number of holes, each 0.344 inch (8.74 mm) in diameter. After coating a hole with adhesive cement, a sleeve to be tested is compressed to permit insertion and then allowed to expand against the adhesive cement. After standing in a room temperature environment (23° C., 48% relative humidity) for at least one day to allow the adhesive cement to cure, the jaw of a tensile tester ("Instron" Model 1122) is clamped either onto a protruding duct of the sleeve or, if there is no duct, onto a portion of an ear piece onto which the sleeve has been fitted. The assembly is then warmed to 37° C., held at that temperature for 3 minutes, and then immediately tested in the room temperature environment by measuring the axial force required to pull the duct or ear piece out of the foam at a rate of about 25.4 cm/min.

Pullout Value

This test is carried out in the same way except as follows: The holes in the aluminum block are reamed (but not polished) to a roughness of 32 microinches (0.8 micrometers) peak-to-valley, and no adhesive is applied to the holes. After standing for at least three minutes, the tensile tester measures the axial force required to pull the sleeve out of the hole.

Retarded Recovery Value

A 8.0-mm cube is cut from the foam and then held for 24 hours at 23° C., 48% relative humidity and tested under those conditions. While standing on an aluminum plate, it is compressed to 1.6 mm using an aluminum piston 19 mm in diameter and immediately released. The time required for it to recover to a height of 6.4 mm is the Retarded Recovery Value of the foam.

EXAMPLE 1

A number of sleeves were made as illustrated in FIG. 7 using unplasticized polyurethane foam identical to that used in the aforementioned "Attenutech" 6300 earplugs. The foam had a Retarded Recovery Value of 27 seconds. When tested according to ANSIA Specifications S3.19-1974, it provided a noise reduction rating of 29 dB. The flexible plastic duct 76 was molded of plasticized poly(vinyl chloride), and the foam was adhered to the duct using plastic adhesive No. 4475 from 3M. Its rigid plastic adapter 79 was polycarbonate. Significant dimensions were:

| | |
|---|---|
| Foam 74 | |
| maximum outer diameter | 12.7 mm |
| length | 15.9 mm |
| Duct 76 | |
| length | 12.7 mm |
| outer diameter | 3.1 mm |
| inner diameter | 1.9 mm |

Using a die punch, the foam of each of the sleeves had been formed with a central passage 3.2 mm in diameter while sometimes simultaneously forming 2, 3 or 4 symmetrically arranged flutes, each 3/16 inch (4.8 mm) in diameter and centered on the maximum circumference of the foam.

A set of four such sleeves including one with no flutes should permit an audiologist to fit 80–90% of potential users while also affording whatever level of venting is desired.

A number of persons have worn such sleeves with their hearing aids, and a majority of them reported enhanced comfort and improved sound quality.

EXAMPLE 2

A number of sleeves were made substantially as illustrated in FIG. 5 using the same foam as was used in Example 1. Using a die punch, the foam was formed with a central passage 2.4 mm in diameter, and flutes were simultaneously formed in some of the sleeves as in Example 1. Each sleeve was self-threaded onto the male screw thread 52 of the ear piece 51 which had been formed of a rigid plastic ("Ultem" from G.E.) as follows:

| | |
|---|---|
| major diameter of thread | 4.6 mm |
| minor diameter of thread | 2.8 mm |
| pitch of thread | 0.55 thread/mm |
| width at crown | 0.25 mm |
| thread profile | |
| of leading (distal) face | 105° |
| of trailing (proximal) face | 95° |

EXAMPLE 3

A number of sleeves were made as illustrated in FIG. 6, except that, for purposes of testing, the duct 66 extended beyond the proximal end of the foam 64. The foam and duct were made from the same materials as were used in Example 1.

| | Testing | |
|---|---|---|
| | Pullout Value (gm force) | Holding Value (gm force) |
| Sleeves of Example 2 | | |
| No flutes | 240 | 2033 |
| 2 flutes | 190 | 1843 |
| 3 flutes | 145 | 1585 |
| 4 flutes | 110 | 1442 |
| Sleeves of Example 3 | | |
| No flutes | 279 | 623 |
| 2 flutes | 176 | NT |
| 3 flutes | 131 | NT |
| 4 flutes | 105 | 189 |

NT = not tested

We claim:

1. Hearing aid comprising an ear piece including a sound tube, a user-disposable sleeve which is formed with distal and proximal ends, a central longitudinal passage between said distal and proximal ends having a size approximating that of said sound tube wherein the sleeve has an exterior surface, comprises soft polymeric foam that is highly compressible, has slow, substantially complete recovery, and can be compressed to be freely insertable into an external ear canal of the user and to become wedged in the canal when the foam is allowed to recover, and fastening means for disposably attaching the proximal end of the sleeve to said ear piece with said passage connecting the sound tube to the ear canal of the user, said fastening means providing a Holding Value and a Pullout Value and wherein said Holding Value is at least $1\frac{1}{2}$ times said Pullout Value.

2. Hearing aid as defined in claim 1 wherein said polymeric foam is a polyurethane foam which is free from plasticizer.

3. Hearing aid as defined in claim 2 wherein said polyurethane foam has a Retarded Recovery Value which is no less than 4 seconds and no more than 45 seconds.

4. Hearing aid as defined in claim 1 which further comprises a duct over which said foam fits and to which the foam is firmly secured, the duct being formed to provide said central passage and said fastening means.

5. Hearing aid as defined in claim 4 wherein said duct comprises a moldable flexible plastic.

6. Hearing aid as defined in claim 4 having a layer of adhesive securing the foam to the duct.

7. Hearing aid as defined in claim 4 wherein said fastening means comprises interlocking means formed on the duct which are adapted to interlock with means on the ear piece.

8. Hearing aid as defined in claim 7 wherein said interlocking means comprise mating screw threads formed on the duct and the ear piece.

9. Hearing aid as defined in claim 8 wherein said screw threads are tapered to guard against cross threading.

10. Hearing aid as defined in claim 8 wherein the duct is formed with a projection extending beyond the proximal end of the foam, and the projection is formed with male screw threads which mate with female screw threads formed on the ear piece.

11. Hearing aid as defined in claim 10 wherein the exterior surface of the foam is formed with at least one flute for venting the ear of the user.

12. Hearing aid as defined in claim 11 wherein the distal end of the ear piece is formed with an annular channel extending arond said sound tube and with a series of air vents, each opening into said annular channel, said at least one flute communicating with said air vents through said annular channel.

13. Hearing aid as defined in claim 7 wherein the interlocking means comprise a ball formed on the ear piece, and a socket formed on the duct which mates with the ball.

14. Hearing aid as defined in claim 1 wherein said fastening means comprises a layer of pressure-sensitive adhesive on a proximal surface of the sleeve, a distal surface of the ear piece having a smooth surface to which said adhesive layer can be releasably adhered.

15. Hearing aid as defined in claim 14 wherein said sleeve comprises a flexible, elongated plastic duct which is formed with said longitudinal passage, and the ear piece has a projection which fits into said duct to align the sleeve and the ear piece.

16. Hearing aid as defined in claim 1 wherein said central passage is flared out at the distal end of the sleeve.

17. A user-disposable sleeve for a hearing aid that comprises an ear piece including a sound tube, said sleeve being freely insertable into an external ear canal of the user and comprising a flexible, elongated duct which is formed with a longitudinal passage and fastening means at one end thereof for disposably attaching the duct to said ear piece with said passage connecting the sound tube of the hearing aid to the ear of the user, soft polymeric foam having proximal and distal ends, said foam fitting over and being firmly secured to the duct, with said fastening means being at said proximal end of said foam, which foam has slow, substantially complete recovery, and can be compressed to be freely insertable into said external ear canal of the user and to become wedged in the canal when the foam is allowed to recover.

18. A user-disposable sleeve as defined in claim 17, the exterior surface of which is formed with at least one flute for venting the user's ear.

19. A user-disposable sleeve as defined in claim 17 wherein the exterior surface of said sleeve comprises a skin of higher density cell structure than that of the interior of said sleeve.

20. A user-disposable sleeve as defined in claim 17 wherein the fastening means comprises interlocking means formed on the duct which are adapted to interlock with means on and the earpiece.

21. A user-disposable sleeve as defined in claim 20 wherein said duct comprises a flexible material and said interlocking means comprises a screw thread.

22. A user-disposable sleeve for a hearing aid, which hearing aid comprises an ear piece including a sound tube, which ear piece is formed with a distal screw thread, said sleeve comprising a flexible, elongated plastic duct which if formed with a longitudinal passage approximating the size of said sound tube and with a proximal screw thread which mates with said screw thread of the ear piece to permit the duct to be detachable secured to the ear piece, soft polymeric foam fitting over and bonded to said plastic duct, which foam has an exterior surface, is highly compressible, has slow, substantially complete recovery, and can be compressed to be freely insertable into an external ear canal of the user and to become wedged in the canal when the foam is allowed to recover.

23. A user-disposable sleeve as defined in claim 22 wherein the exterior surface of the foam is substantially cylindrical and formed with at least one flute to vent the user's ear.

24. A kit of user-disposable sleeves for insertion into an external ear canal of the user, each comprising an ear piece including a sound tube, which ear piece is formed with a distal screw thread, each of said sleeves comprising a flexible, elongated plastic duct which is formed with a longitudinal passage having a size approximating that of said sound tube and with a proximal screw thread which mates with said screw thread of the ear piece to permit the duct to be detachably secured to the ear piece, soft polymeric foam fitting over and bonded to said plastic duct, which foam has an exterior surface, is highly compressible, has slow, substantially complete recovery, and can be compressed to be freely insertable into the external ear canal of the user and to become wedged in the canal when the foam is allowed to recover, at least some of said sleeves having one or more flutes formed in their said exterior surface for venting the ear of the user, thereby enabling almost everyone to be fitted.

25. A user-disposable sleeve for a hearing aid, which hearing aid comprises an ear piece including a sound tube, said sleeve having distal and proximal ends and comprising soft polymeric foam which is highly compressible, has slow, substantially complete recovery, and can be compressed to be freely insertable into an external ear canal of the user and to become wedged in the canal when the foam is allowed to recover, the foam having a substantially cylindrical exterior surface which is formed with at least one flute to vent the ear of the user, a flexible, elongated duct over which the foam fits and to which the foam is firmly secured, and fastening means for disposably attaching the proximal end of the sleeve to said ear piece.

26. A user-disposable sleeve as defined in claim 25, there being at least 2 symmetrically arranged flutes.

27. A user-disposable sleeve as defined in claim 19, wherein the exterior surface of said sleeve comprises a skin of higher density cell structure than that of the remainder of said sleeve.

28. A user-disposable sleeve as defined in claim 25 wherein the exterior surface of said sleeve comprises a skin of higher density cell structure than that of the interior of said sleeve.

29. A user-disposable sleeve as defined in claim 25 having at least two separate flutes.

30. a kit of user-disposable sleeves for insertion into an external ear canal of the user, each of said sleeves having proximal and distal ends and comprising soft polymeric foam which is highly compressible, has slow, substantially complete recovery, and can be compressed to be freely insertable into the external ear canal of the user and to become wedged in the canal when the foam is allowed to recover, the foam having a substantially cylindrical exterior surface, fastening means at said proximal end of the sleeves for disposably attaching the sleeve to said ear piece, at least some of said sleeves having one or more flutes formed in said exterior surface for venting the ear of the user, thereby enabling almost everyone to be fitted.

31. A sleeve adapted for use with a hearing aid having an ear piece including a sound tube, said sleeve comprising an external surface, a substantially cylindrical body, a central passage through said body, a fastening means for disposably attaching said sleeve to said hearing aid, said fastening means providing a Holding Value and a Pullout Value, wherein said Holding Value is at least $1\frac{1}{2}$ times said Pullout Value, and at least one flute on the external surface of said body, said sleeve being made from a retarded recovery foam.

32. A sleeve as defined in claim 31 wherein said flute extends longitudinally along said exterior surface of said sleeve.

33. A sleeve as defined in claim 32 having at least two of said flutes.

34. A sleeve according to claim 31 made from a foam having a Retarded Recovery Value of at least 4 seconds and no more than 45 seconds.

35. A sleeve according to claim 34 wherein said Retarded Recovery Value is at least 15 seconds and no more than 35 seconds.

36. A disposable sleeve adapted for insertion into an external ear canal of a user to facilitate transmission of sound to the ear of the user comprising soft polymeric foam having proximal and distal ends, and longitudinal passage there between, a hollow, flexible, elongated duct firmly secured in said longitudinal passage, wherein said foam has an exterior surface, is highly compressible, has slow, substantially complete recovery, and can be compressed to be freely insertable into said external ear canal of said user to become wedged in the canal when the foam is allowed to recover, and means fastened to the proximal end of said foam for disposably attaching said sleeve to a sound transmission device.

37. A disposable sleeve as defined in claim 36 having at least one flute formed in said exterior surface.

38. A disposable sleeve as defined in claim 37 having at least two flutes formed in said exterior surface.

39. A disposable sleeve as defined in claim 38 wherein said flutes are symmetrically arranged in said exterior surface.

40. A disposable sleeve having proximal and distal ends and which is adapted for use with a sound transmission device, said sleeve comprising a flexible duct having a passage therethrough, a soft, retarded recovery polymeric foam around and securely attached to said duct, and means for fastening said sleeve to said transmission device at said proximal end.

41. A disposable sleeve as defined in claim 40 having an exterior surface with at least one flute formed therein.

42. A disposable sleeve as defined in claim 41 having at least two flutes formed in said exterior surface.

43. A disposable sleeve as defined in claim 42 wherein said flutes are symmetrically arranged in said exterior surface.

* * * * *

UNITED STATES PATENT AND TRADEMARK OFFICE
CERTIFICATE OF CORRECTION

PATENT NO. : 4,880,076

DATED : November 14, 1989

INVENTOR(S) : Carl S. Ahlberg, Davis W. Chamberlin, Jerold W. Bushong, Robert J. Oliveira and Vasant V. Kolpe It is certified that error appears in the above-identified patent and that said Letters Patent is hereby corrected as shown below:

Col. 1, line 22, "1,743,817" should be --1,753,817--.

Col. 3, line 11, "hearng" should be --hearing--.

Col. 6, line 47, "ANSIA" should be --ANSI--.

Col. 8, line 36, "arond" should be --around--.

Col. 10, line 13, the reference to claim "19" should be to claim --22--.

Signed and Sealed this

Twelfth Day of March, 1991

*Attest:*

HARRY F. MANBECK, JR.

*Attesting Officer* *Commissioner of Patents and Trademarks*